United States Patent [19]

Smirmaul

[11] Patent Number: 4,766,897
[45] Date of Patent: Aug. 30, 1988

[54] CAPSULECTOMY SURGICAL INSTRUMENT

[76] Inventor: Heinz Smirmaul, 1307 Brookstone La., Duncanville, Tex. 75137

[21] Appl. No.: 62,865

[22] Filed: Jun. 16, 1987

[51] Int. Cl.⁴ ............................................. A61B 17/32
[52] U.S. Cl. ...................................... 128/305; 30/263; 30/276
[58] Field of Search .......... 604/22; 128/305, 751–755, 128/305.1, 310; 30/263, 272 R, 276, 274

[56] References Cited

U.S. PATENT DOCUMENTS

| 3,990,453 | 11/1976 | Douvas et al. | 128/305 |
| 4,320,761 | 3/1982 | Haddad | 128/305 |
| 4,336,805 | 6/1982 | Smirmaul | 128/310 |
| 4,423,728 | 1/1984 | Lieberman | 128/310 |
| 4,429,696 | 2/1984 | Hanna | 128/310 |
| 4,436,091 | 3/1984 | Banko | 128/305 |

FOREIGN PATENT DOCUMENTS

81/03122 11/1981 PCT Int'l Appl. ................ 128/305

Primary Examiner—Michael H. Thaler
Attorney, Agent, or Firm—Richards, Harris, Medlock & Andrews

[57] ABSTRACT

An ophthalmic surgical instrument (10) is provided for incising the anterior lens capsule of the crystalline lens of an eye. The surgical instrument (10) includes a handle (12) adapted for support in a hand of a user. A tubular member (16) extends from the handle (12) and terminates in a loop (18). A circular cutting device (20) is rotatably mounted within the loop (18). A flexible elongate wire (24) is disposed within the tubular member (16) and is interconnected to the circular cutting device (20) and the handle (12) such that the circular cutting device (20) is rotated upon compression of the handle (12).

6 Claims, 2 Drawing Sheets

CAPSULECTOMY SURGICAL INSTRUMENT

TECHNICAL FIELD

This invention relates to surgical instruments, and more particularly to an ophthalmic surgical device for cutting the anterior lens capsule required in extracapsular cataract surgery.

BACKGROUND ART

In performing ophthalmic extracapsular cataract surgery an opening must be provided in the anterior lens capsule of the eye through which the cataract is removed. This procedure involves the removal of the crystalline lens substance after opening or excising the anterior lens capsule.

Several methods have been utilized for opening the anterior lens capsule. An early method was needling or incising the membrane with multiple, slashing incisions made with a knife, needle or a scythe-like instrument called a cystotome. Another early technique involved grasping the anterior capsule with forceps and tearing off a piece of the capsule. A dull cystotome method has been utilized in which the anterior capsule is engaged opposite the entry site and is torn in one movement toward the surgeon, creating a triangular flap which is pulled out of the eye and then excised.

In recent years, many alternative capsulectomy methods have been proposed. Common to these methods has been the desire to increase the control of the excision with less emphasis on tearing and ripping. It is also recognized that endosurgical capsulectomy is desirable in order to visualize the capsule and avoid damage to adjacent intraocular tissue since the tissue which surrounds the endothelium of the cornea is sensitive to being touched, and the vision can be destroyed if the tissue around this space is traumatized. Thus, surgical instrumentation which is employed must be small in size. A technique widely utilized is known as the "can opener" method in which a hypodermic needle having its bevel bent to the shaft is used to make small triangular tears along the desired line of excision. The central piece of the anterior lens capsule is then grasped with a small forcep and is torn away along the perforations. However, since the anterior lens capsule is similar to a cellophane wrapping material, once a tear is initiated in an undesirable direction, the capsule may tear to the edge, resulting in a loss of structural stability of the membrane which often allows vitreous to spill into the anterior chamber.

Therefore, a need exists for a surgical instrument that allows for controlled incisions rather than unpredictable ripping or tearing and which allows the surgeon to obtain precise placement of the instrument for excision of the anterior lens capsule.

DISCLOSURE OF THE INVENTION

In accordance with the present invention, an ophthalmic surgical instrument is provided for substantially eliminating the problems heretofore associated with instruments for incising the anterior lens capsule of the crystalline lens of an eye.

In accordance with the present invention, an ophthalmic surgical instrument includes a handle adapted for support in the hand of user. A shaft extends from the handle. The cutting device is mounted to the shaft opposite the handle. Structure is disposed within the shaft interconnecting the cutting device and the handle, such that the cutting device is rotated upon compression of the handle.

In accordance with another aspect of the present invention, an ophthalmic surgical instrument for incising the anterior lens capsule of the crystalline lens of an eye is provided. The instrument includes a handle adapted for support in a hand of a user. An elongated tubular member having first and second ends is attached to the handle at the first end thereof. The second end is terminated in a loop. A circular cutting blade is interconnected to the loop for rotation therein. A flexible elongate wire having first and second ends is disposed within the tubular member. The first end of the wire is interconnected to the handle and the second end of the wire is interconnected to the circular cutting blade. Upon compression of the handle, the wire is retracted within the handle for rotating the cutting blade around a predetermined angle.

BRIEF DESCRIPTION OF THE DRAWINGS

For a more complete understanding of the present invention and for further advantages thereof, reference is now made to the following Detailed Description taken in conjunction with the accompanying Drawings in which.

DETAILED DESCRIPTION

Figure 1:
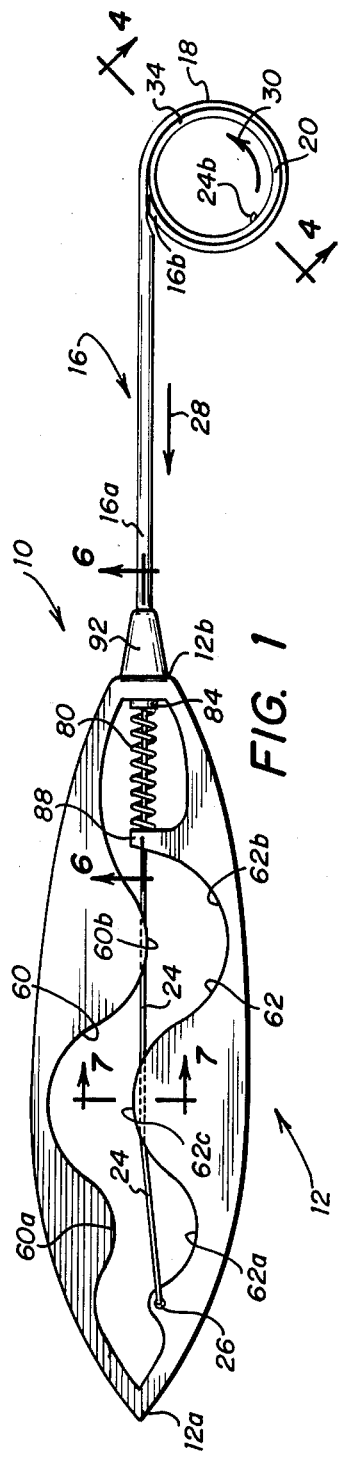
FIG. 1 is a top plan view of the present capsulectomy surgical instrument, with the handle partially broken away to illustrate the interior of the handle.
Figure 2:
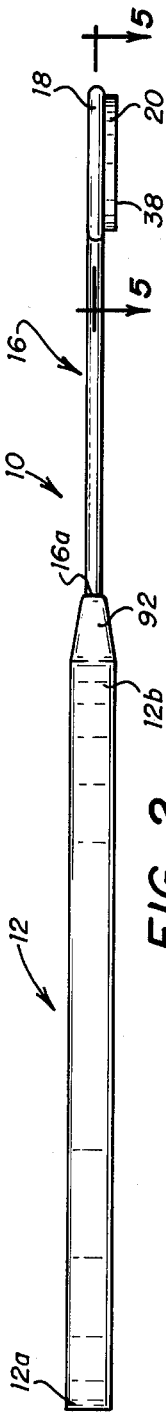
FIG. 2 is a side elevational view of the present capsulectomy surgical instrument.

Referring simultaneously to FIGS. 1 and 2, the present capsulectomy surgical instrument is illustrated and is generally identified by the numeral 10. Surgical instrument 10 includes a handle generally identified by the numeral 12 having ends 12a and 12b. Interconnected to end 12b of handle 12 is an elongated tubular member, generally identified by the numeral 16. Tubular member may comprise, for example, a hollow hypodermic needle, 16–18 gauge. Tubular member 16 includes ends 16a and 16b. A loop 18 is formed adjacent to end 16b of tubular member 16 and forms a support for a circular cutting blade 20. As will be further described, circular cutting blade 20 is rotatable within loop 18 upon operation of handle 12 of surgical instrument 10. Circular cutting blade 20 forms a circular incision in the anterior lens capsule for easy removal of the anterior lens capsule during extracapsular cataract surgery. The cut is clean leaving no free tags of tissue.

Figure 5:
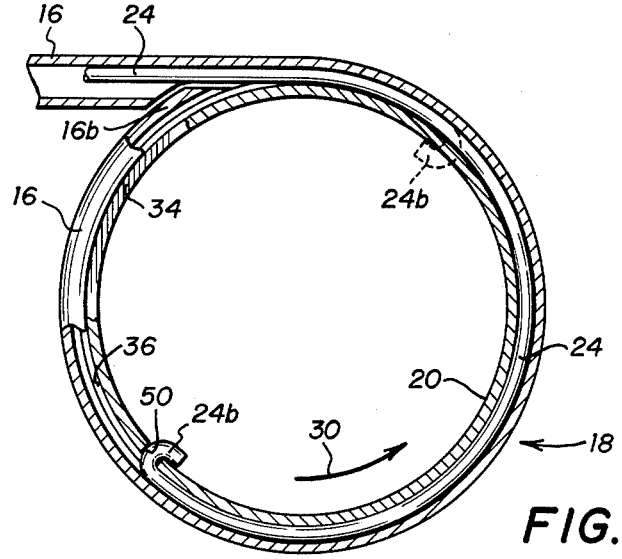
FIG. 5 is a cross-sectional view of the present circular cutting blade and tubular loop support taken generally along sectional lines 5—5 of FIG. 2.

Rotation of circular cutting blade 20 is accomplished through the use of a flexible elongate wire, generally identified by the numeral 24. Flexible elongate wire 24 may have a diameter of, for example, 0.005 inches and includes ends 24a and 24b (FIG. 5). Flexible elongate wire 24 extends throughout handle 12, tubular member 16 and loop 18. End 24a of flexible elongate wire 24 is attached to handle 12 at point 26 (FIG. 1). As will subsequently be described, by retracting flexible elongate wire 24 within handle 12 in the direction of arrow 28, circular cutting blade 20 is caused to rotate in the direction of arrow 30 to effectuate cutting.

Figure 3:
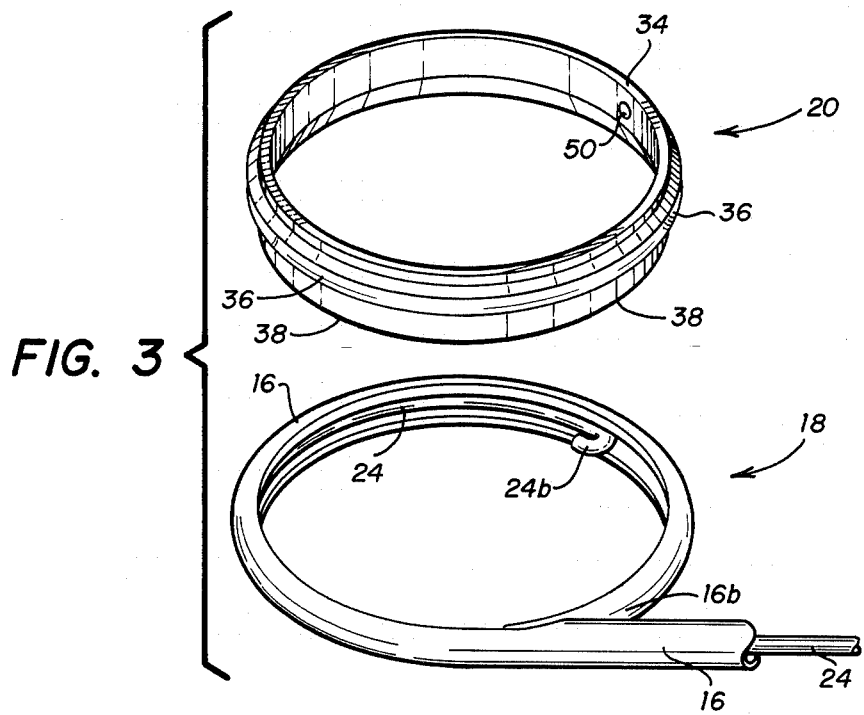
FIG. 3 is an exploded perspective view of the present circular cutting blade and tubular loop support for the circular cutting blade.
Figure 4:
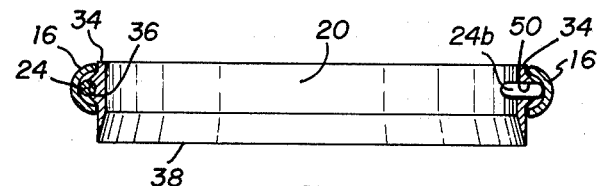
FIG. 4 is a cross-sectional view of the present circular cutting blade and tubular loop support taken generally along sectional lines 4—4 of FIG. 1.

Referring now simultaneously to FIGS. 3, 4 and 5, wherein like numerals are utilized for like and corresponding components previously identified, circular cutting blade 20 is received within loop 18 for slidable movement therein. As more clearly illustrated in FIG. 3, circular cutting blade 20 includes a central portion 34, a side flange 36 and a cutting edge 38. Side flange 36 engages loop 18 such that circular cutting blade 20 is free to rotate within the confines of tubular loop 18. Tubular member 16 in the area of loop 18 has the interior portion thereof removed around the entire inner circumference of loop 18. Circular cutting blade 20 is about 1 mm to 2 mm in height and about 6 mm in diameter.

Referring to FIGS. 4 and 5, circular cutting blade 20 is interconnected to flexible elongate wire 24 by passing end 24b through an aperture 50 within circular cutting blade 20. Through this connection, movement of flexible elongate wire 24 towards or away from handle 12 results in a circular movement of cutting blade 20 within loop 18. FIG. 5 illustrates two positions of flexible elongate wire 24 and circular cutting blade 20. End 24b of flexible elongate wire 24 is shown in dotted lines and indicates a rotated position of circular cutting blade 20 in the direction of arrow 30 from the position shown in solid lines which is also shown in FIG. 3.

During assembly of the present capsulectomy surgical instrument 10, flexible elongate wire 24 is inserted in tubular member 16 and circular cutting member 20 is inserted within loop 18. End 24b of flexible elongate wire 24 is then inserted through aperture 50 of circular cutting blade 20.

Figure 7:
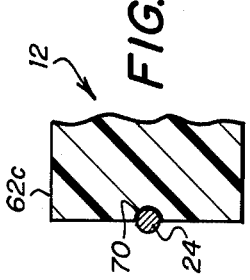
FIG. 7 is a cross-sectional view of a portion of the handle of the present capsulectomy surgical instrument taken generally along sectional lines 7—7 of FIG. 1.
Figure 6:
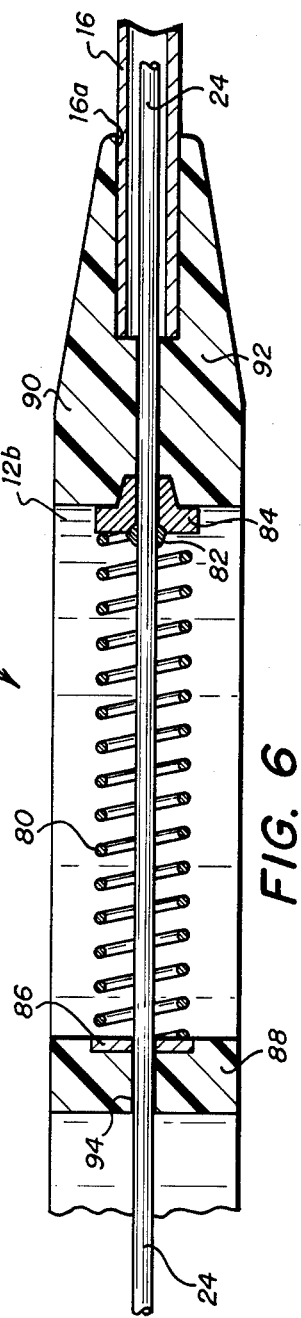
FIG. 6 is a cross-sectional view of a portion of the handle of the present capsulectomy surgical instrument taken generally along sectional lines 6—6 of FIG. 1.

Referring again to FIG. 1 and also to FIGS. 6 and 7, the structure for controlling the movement of flexible elongate wire 24 within tubular member 16 will now be discussed. As shown in FIG. 1, the interior of handle 12 includes an upper curvalinear surface 60 having ridges 60a and 60b. Upper curvalinear surface 60 mates with a lower curvalinear surface 62 having grooves 62a and 62b adjacent ridges 60a and 60b. Flexible elongate wire 24 is positioned within handle 12 between upper curvalinear surface 60 and lower curvalinear surface 62 such that upon compression of handle 12, upper curvalinear surface 60 and lower curvalinear surface 62 approach each other such that the intermediately disposed flexible elongate wire 24 conforms to the curves of surfaces 60 and 62 thereby drawing flexible elongate wire 24 into handle 12. Flexible elongate wire 24 is compressed into grooves 62a and 62b of lower curvalinear surface 62 and flexible elongate wire 24 is thereby retracted into handle 12. Lower curvalinear surface 62 also includes a ridge 62c including a guideway 70 as more clearly shown in FIG. 7 for maintaining the position of flexible elongate wire 24 between upper and lower curvalinear surfaces 60 and 62, respectively.

Flexible elongate wire 24 is biased to handle 12 utilizing a spring 80 which returns flexible elongate wire 24 to a nonretracted position after decompression of handle 12. Spring 80 is integrally attached to wire 24 utilizing a weld 82 (FIG. 6). Spring 80 is disposed between an end cap 84 and a seat 86 of an end block 88 which is integrally formed with handle 12. End cap 84 mates with a seat 90 in a closure member 92 positioned at the end 12b of handle 12. Upon retraction of wire 24 within handle 12, spring 80 is compressed against end block 88, and end cap 84 moves towards end 12a of handle 12. When handle 12 is released, spring 80 expands to move flexible elongate wire 24 outwardly of handle 12 such that end cap 84 reengages seat 90 of closure member 92. Flexible elongate wire 24 passes through an aperture 94 within end block 88.

Although FIG. 1 illustrates the use of upper and lower curvalinear surfaces 60 and 62 for retracting wire flexible elongate wire 24 within handle 12, other structures may be suggested to one skilled in the art to accomplish this function, and the present invention is not limited to the configuration shown in FIG. 1 for effecting a retraction of flexible elongate wire 24. Handle 12 may be composed of any flexible type material such as, for example, plastic or rubber. Further, tubular member 16 may be bent to facilitate insertion of surgical instrument 10 into the eye.

It therefore can be seen that the present capsulectomy surgical instrument is easy to manufacture and operate, and operates to create a circular incision in the anterior lens capsule. The compression of the handle of the present surgical instrument causes lateral motion of the wire extending through the handle to the circular cutting blade and imparts rotational motion to the circular cutting blade. By repeated compressions of the handle, the circular cutting blade is caused to rotate back and forth to create the desired depth of the incision for incising the anterior lens capsule.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. An ophthalmic surgical instrument for incising the anterior lens capsule of the crystalline lens of an eye comprising:
   a handle adapted for support in a hand of a user;
   a elongated tubular means having first and second ends, said first end being attached to said handle and said second end terminating in a loop;
   a circular cutting blade interconnected to said loop, such that said circular cutting blade is supported by and is rotatable within said loop; and
   a flexible elongate wire having first and second ends and being disposed within said elongated tubular member, said first end thereof being interconnected to said handle and said second end thereof being interconnected to said circular cutting blade, such that upon compression of said handle, said wire is retracted within said handle for rotating said cutting blade around a predetermined angle within said loop.

2. The ophthalmic surgical instrument of claim 1 wherein said handle further includes:
   means for temporarily deforming said flexible elongate wire within said handle to cause said flexible elongate wire to be retracted within said handle.

3. The ophthalmic surgical instrument of claim 1 wherein said handle includes:

means for biasing said flexible elongate wire to return said flexible elongate wire to a nonretracted position.

4. An ophthalmic surgical instrument for incising the anterior lens capsule of the crystalline lens of an eye comprising:
   a handle adapted for support in a hand of a user;
   a elongated tubular member having first and second ends, said first end being attached to said handle and said second end terminating in a loop;
   said tubular member loop including a slotted aperture;
   a circular cutting blade slidably mounted within said loop for rotation therein;
   a flexible elongate wire having first and second ends and being disposed within said tubular member, said first end thereof being interconnected to said handle and said second end thereof being interconnected to said circular cutting blade;
   means for attaching said flexible elongate wire second end to said cutting blade, such that upon compression of said handle, said flexible elongate wire is retracted within said handle to cause rotation of said cutting blade within said loop around a predetermined angle.

5. The ophthalmic surgical instrument of claim 4 and further including:
   biasing means attached to said handle and to said flexible elongate wire for urging said flexible elongate wire to a nonretracted position after compression of said handle.

6. The ophthalmic surgical instrument of claim 4 wherein said slotted aperture extends for approximately the entire circumference of said loop.

* * * * *